United States Patent
Delache et al.

(10) Patent No.: US 6,644,310 B1
(45) Date of Patent: Nov. 11, 2003

(54) APPARATUS AND METHOD FOR PROVIDING A BREATHING GAS EMPLOYING A BI-LEVEL FLOW GENERATOR WITH AN AC SYNCHRONOUS MOTOR

(75) Inventors: Alain J. Delache, Nice (FR); Jacques Souquet, Nice (FR); Paul F. Emerson, St. Louis Park, MN (US); James L. Campbell, Plymouth, MN (US)

(73) Assignee: Mallinckrodt Inc., St. Louis, MO (US)

( * ) Notice: Subject to any disclaimer, the term of this patent is extended or adjusted under 35 U.S.C. 154(b) by 265 days.

(21) Appl. No.: 09/672,710

(22) Filed: Sep. 29, 2000

(51) Int. Cl.[7] .............................................. A61M 16/00
(52) U.S. Cl. ............................... 128/204.21; 128/204.18
(58) Field of Search ....................... 128/204.18, 204.19, 128/204.21, 204.23, 204.26, 205.18, 205.13, 205.14, 205.24, 205.25; 165/58, 59, 108, 120, 80.2; 361/690, 691, 694, 695

(56) References Cited

U.S. PATENT DOCUMENTS

| | | | | |
|---|---|---|---|---|
| 4,290,108 A | * | 9/1981 | Woehrle et al. ............... 364/480 |
| 4,348,734 A | * | 9/1982 | Dougherty ................... 364/721 |
| 4,599,550 A | | 7/1986 | Robertson, Jr. et al. | |
| 5,368,019 A | * | 11/1994 | Latorraca ................ 128/204.18 |
| 5,433,193 A | * | 7/1995 | Sanders et al. ......... 128/204.18 |
| 5,495,160 A | * | 2/1996 | Pond .......................... 318/801 |
| 5,577,496 A | * | 11/1996 | Blackwood et al. ... 128/201.25 |
| 5,845,636 A | * | 12/1998 | Gruenke et al. ........ 128/204.21 |
| 5,865,173 A | * | 2/1999 | Froehlich ................ 128/204.21 |
| 6,029,660 A | * | 2/2000 | Calluaud et al. ........ 128/200.21 |
| 6,050,260 A | * | 4/2000 | Daniell et al. .......... 128/203.12 |
| 6,152,129 A | * | 11/2000 | Berthon-Jones ........ 128/200.24 |
| 6,240,921 B1 | * | 6/2001 | Brydon et al. .......... 128/204.18 |
| 6,302,105 B1 | * | 10/2001 | Wickham et al. ....... 128/200.27 |
| 6,332,463 B1 | * | 12/2001 | Farrugia et al. ........ 128/204.18 |
| 6,345,619 B1 | * | 2/2002 | Finn ....................... 128/204.18 |
| 6,349,724 B1 | * | 2/2002 | Burton et al. ........... 128/204.18 |
| 6,367,474 B1 | * | 4/2002 | Berthon-Jones et al. ...................... 128/204.23 |
| 6,401,713 B1 | * | 6/2002 | Hill et al. ............... 128/204.21 |
| 2002/0114536 A1 | * | 8/2002 | Richey, II ............... 128/204.22 |

FOREIGN PATENT DOCUMENTS

| | | |
|---|---|---|
| EP | 0 661 071 A1 | 7/1995 |
| WO | WO 92/11054 A1 | 7/1992 |
| WO | WO 97/02064 A1 | 1/1997 |

* cited by examiner

*Primary Examiner*—Weilun Lo
*Assistant Examiner*—Teena Mitchell
(74) *Attorney, Agent, or Firm*—Rothwell, Figg, Ernst & Manbeck PC (57) ABSTRACT

An apparatus and method for treating sleep apnea includes a bilevel flow generator having an alternating current (AC) synchronous motor coupled to a low inertia centrifugal rotor/impeller. The process of acceleration and deceleration of the rotor involves moving from frequency A, amplitude A to frequency B, amplitude B in an optimal linear fashion using the so-called Bresenham algorithm. This is coupled with a tuned increase of the amplitude during the acceleration process which will produce the acceleration using minimum current allowing the use of smaller power supplies. During deceleration the process is accomplished in reverse fashion using a tuned decrease of the amplitude coupled with a special shunt circuit to prevent power supply voltage changes. These changes in amplitude overlay a current feedback mechanism used to prevent loss of synchronization of the motor by changing amplitude. Speed changes can also be timed so as to prevent desynchronization.

22 Claims, 10 Drawing Sheets

APPARATUS AND METHOD FOR PROVIDING A BREATHING GAS EMPLOYING A BI-LEVEL FLOW GENERATOR WITH AN AC SYNCHRONOUS MOTOR

BACKGROUND OF THE INVENTION

1. Field of the Invention

The present invention relates to an apparatus and method for delivering a breathing gas to a user at alternating levels of pressure as a treatment for respiratory conditions such as sleep apnea.

2. Discussion of the Background Art

The sleep apnea syndrome affects some 1% to 5% of the general population and is due to upper airway obstruction during sleep. The direct consequences of sleep apnea are sleep fragmentation, partial cessation of ventilation and oxyhemoglobin desaturation. These in turn translate into daytime somnolence, cardiac arrhythmia, congestive heart failure and a variety of other health as well as cognitive dysfunctions. All of these have secondary social and behavioral effects which can result in increased patient morbidity as well as possible mortality if they are engaged in activities which require alertness (such as driving a car).

The causes of upper airway obstruction are varied but may include anatomical changes leading to a narrowing of the pathway, loss of muscle tone and/or increased weight of the structures. Age and obesity appear to be risk factors suggesting that an excess of soft tissue in the neck may provide sufficient pressure on internal structures to compromise the patency of the airway.

Treatment has involved a variety of surgical interventions including uvulopalatopharyngoplasty, gastric surgery for obesity, maxillo-facial reconstruction or even tracheostomy. All of these procedures have the risk of significant morbidity. A more benign treatment but one which requires some behavioral adjustment is that of nasal continuous positive airway pressure (nCPAP or just CPAP). In its simplest form, this treatment involves applying positive pressure to the airway using an airflow generator to force the passage to remain open. If used consistently during sleep, symptoms of sleep apnea can be successfully mitigated.

Some patients, however, are nonresponsive or noncompliant with CPAP treatment due to its continuous nature. This is especially true if the CPAP prescription pressure is relatively high. For these individuals a bilevel therapy is a more reasonable alternative. Pressure cycles from a high level during inhalation (IPAP) to a low level (EPAP) to facilitate exhalation while at the same time continuing to provide some nominal pressure support. This is also useful for individuals who have some form of compromised respiration such as a weakness of the diaphragm muscle due to disease or spinal injury where continuous pressure may be problematic.

In accomplishing the IPAP to EPAP switch several techniques have been used by the prior art. Some examples include the use of weighted bellows, pressure-reducing valves coupled to pneumatic sources, constant speed blowers coupled with valving, injector drives, linear driven pistons, nonlinearly driven pistons, and spring loaded bellows. Most systems have used constant speed blowers coupled with valving to effect rapid pressure changes requiring minimal energy. Typically the blower will rotate to a speed sufficient to provide the higher IPAP pressure and adjust the pressure downwards using a solenoid controlled exhaust valve. The valve position is changed by a small amount to compensate for increased flow demand and by a large amount to shunt air away from the patient and drop the pressure to EPAP levels.

Variable speed blowers have not typically been used for bilevel flow generators heretofore for several reasons. First, the mass of the blower-motor assembly prevents its rapid acceleration and deceleration which in turn causes suboptimal performance with respect to the work of breathing (i.e., the inhalation or exhalation of a given patient is not supported in real time). Second, off-the-shelf motor controllers are typically not suitable for rapid blower performance and typically require external sensing devices (e.g., hall effect sensors) adding to cost. Third, variable speed motors are traditionally direct current (DC) motors which dissipate large amounts of heat thereby requiring a means of heat dissipation and making miniaturization of the device more difficult.

The current invention makes it possible to employ a variable speed blower in a bilevel flow generator through the use of a microprocessor-controlled alternating current (AC) synchronous permanent magnet motor coupled to a low inertia centrifugal impeller and powered by a low wattage constant voltage switching power supply. The device will rotate the impeller at the rotational frequency of its field which may be changed in accordance with the interrupt rate of a timer circuit in the microprocessor. A method of changing rapidly from one frequency to another without using sensors while maintaining proper operation of the system is also the subject of this disclosure. A method whereby field current may be related to system variables (i.e. flow) will also be disclosed.

SUMMARY OF THE INVENTION

A first aspect of the present invention is generally characterized in an apparatus for delivering a breathing gas to a user including a blower having an alternating current (AC) motor and an impeller rotated by the AC motor to deliver a breathing gas to a user, and a blower control system providing a control signal of variable frequency and amplitude to the AC motor. The frequency and amplitude of the control signal are adjusted periodically by the blower control system to cause operation of the AC motor to alternate between an inhalation mode wherein the impeller is rotated at a first speed generating an inhalation positive airway pressure and an exhalation mode wherein the impeller is rotated at a second speed generating an exhalation positive airway pressure. The blower control system preferably includes a microcontroller which generates a plurality of control signals in the form of pulse width modulated signals having sinusoidally weighted duty cycles. The microcontroller preferably also includes a compare unit with a timer and a plurality of compare registers so that the sinusoidally weighted pulse width modulated signal can be created based on a comparison of a timer value with a compare register value retrieved from a memory device. The compare timer preferably has a variable interrupt rate defining a frequency of the pulse width modulated signal. The amplitude and frequency of the pulse width modulated signals are preferably adjusted by the microcontroller using the Bresenham algorithm.

A second aspect of the present invention is generally characterized in a method of generating bilevel positive airway pressure for respiratory therapy using a gas flow generator having a blower powered by an alternating current (AC) motor. The method includes the steps of applying a motor control signal having an amplitude and a frequency to the motor to produce a blower speed, determining whether a speed change is required for the blower, determining a target amplitude and a target frequency corresponding to a target speed, and adjusting the amplitude and frequency of the motor control signal in steps until the amplitude and frequency correspond with the target amplitude and the target frequency. One of the amplitude and frequency is incremented at a first step interval and the other is incremented at a second step interval which is a multiple of the first step interval, for example using the Bresenham algorithm. Preferably, the method also includes the steps of adding excess amplitude before adjusting the motor control signal and removing the excess amplitude after the target frequency has been achieved so as to maintain synchronization.

In a preferred embodiment, the invention utilizes a low inertia permanent magnet synchronous three-phase AC motor that is supplied by pulse width modulated (PWM) pulses that resemble a sine wave of varying frequency and amplitude. The process of acceleration and deceleration involves moving from frequency A, amplitude A to frequency B, amplitude B in an optimal linear fashion, preferably using the so-called Bresenham algorithm. This is preferably coupled with a tuned increase of the amplitude during the acceleration process that will produce the acceleration using minimum current. During deceleration the process can be accomplished in reverse fashion using a tuned decrease of the amplitude coupled with a special shunt circuit to prevent power supply voltage changes. These changes in amplitude overlay a current feedback mechanism used to prevent loss of synchronization of the motor by changing amplitude. Speed changes are also preferably timed so as to prevent desynchronizations.

The above and other features and advantages of the present invention will be further understood from the following description of the preferred embodiments thereof, taken in conjunction with the accompanying drawings in which like numerals denote like parts.

DETAILED DESCRIPTION OF THE PREFERRED EMBODIMENT

Figure 1:
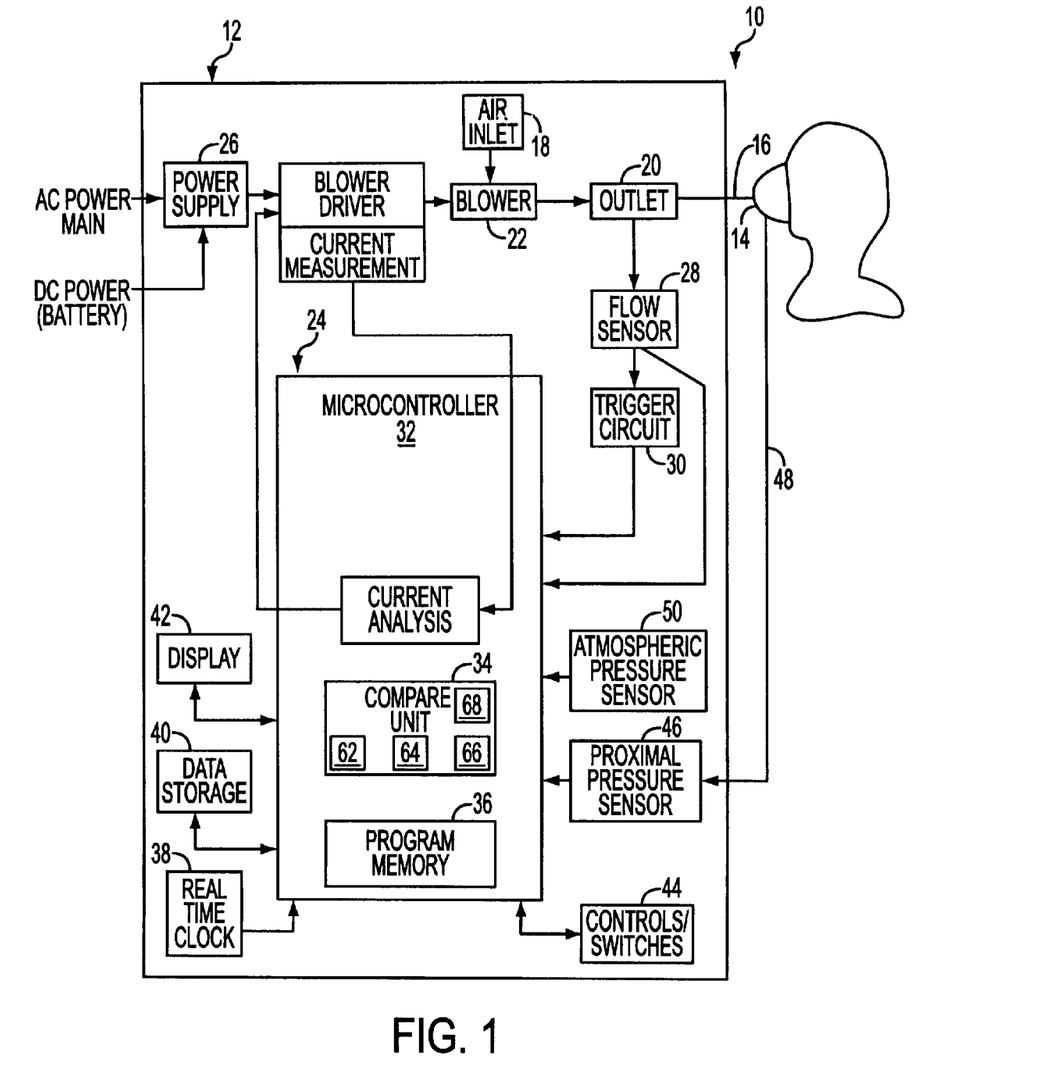
FIG. 1 is a schematic diagram of an apparatus including a gas flow generator with a microcomputer-controlled AC motor according to the present invention.

An apparatus 10 according to a preferred embodiment of the present invention is shown in schematic form in FIG. 1. Apparatus 10 is operable according to a process that is another aspect of the present invention for delivering a breathing gas such as air to a patient at alternating levels of pressure as a treatment for respiratory conditions such as sleep apnea.

Apparatus 10 includes a gas flow generator 12 that receives breathing gas from a source and delivers the gas at alternating levels of positive pressure to a breathing appliance 14 via a delivery conduit 16 such as a hose. The breathing gas can be supplied by any suitable source including, by way of example, ambient air or a pressurized bottle containing a breathing gas. The breathing appliance can be a nose mask, a face mask, a nasal cannula, a tracheostomy tube, or any other suitable appliance for interfacing between a source of breathing gas and a patient's respiratory system. An exhaust port (not shown) is typically provided as part of the breathing appliance or delivery conduit to purge breathing gases during exhalation. Any suitable exhaust port can be used including, by the way of example, conventional valve designs and open ports.

Gas flow generator 12 generally includes a breathing gas inlet 18, a breathing gas outlet 20, a blower 22 receiving breathing gas from the inlet and having an impeller driven by a variable speed motor to deliver the gas at a positive pressure to the outlet, and a blower control system 24 controlling the pressure of breathing gas in the delivery conduit by adjusting the speed of the motor. The gas flow generator preferably also includes a power supply 26 for distributing power from internal or external sources to the blower and blower control system, and a flow meter 28, preferably located downstream of the blower, for generating a flow rate signal indicative of the flow of breathing gas from the blower. The flow rate signal from flow meter 28 is fed to blower control system and is additionally fed to a conventional trigger or decision circuit 30 that uses the flow rate signal in a known manner to provide a trigger signal to the blower control system for initiating a change in motor speed. Gas flow generator 12 is also shown having a proximal pressure sensor 46 which senses gas pressure in a line 48 from mask 14 and provides a signal indicative of mask pressure to blower control system 24, and an atmospheric pressure sensor 50 which provide a signal indicative of atmospheric pressure to the blower control system.

The blower motor is preferably a three-phase synchronous alternating current (AC) motor having a rotor/impeller with permanent magnets and a stator with three windings. Application of three-phase alternating current to the windings generates a rotating magnetic field in the air gap between the rotor and stator. The rotor then revolves synchronously with the speed of the rotating field.

To control the speed of the motor, blower control system 24 preferably includes a microcontroller 32 programmed to generate three sinusoidally weighted pulse width modulated (PWM) signals which are 120 degrees out of phase to produce a rotating field when applied to respective windings of the AC motor. While AC motors are typically operated at a constant speed, the microcontroller of the present invention is programmed to vary the pressure of the breathing gas in an alternating manner at the outlet by alternatingly accelerating and decelerating the motor. Microcontroller 32 is of conventional design with a compare unit 34 and program memory 36. A clock 38 and external data storage 40 are also shown in communication with the microcontroller. The process of acceleration and deceleration involves modifying the PWM signals by moving from frequency A, amplitude A to frequency B, amplitude B in an optimal linear fashion, preferably using the so-called Bresenham algorithm. This is preferably coupled with a tuned increase of the PWM signal amplitude during the acceleration process that will produce the acceleration using minimum power supply current. During deceleration the process can be accomplished in reverse fashion using a tuned decrease of the amplitude coupled with a special shunt circuit to prevent power supply voltage changes. These changes in amplitude overlay a current feedback mechanism used to prevent loss of synchronization of the motor by changing amplitude. When implemented with a low inertia (e.g., less than $5 \times 10^{-6}$ kg-m$^2$) rotor/impeller assembly, the apparatus and method according to the present invention can achieve rapid pressure changes suitable for bilevel positive airway pressure therapy without the use of special valves or sensors. In a preferred embodiment, the invention is implemented in a system having a blower with an impeller formed of a plastic material, such as a 30% glass-filled Noryl plastic.

Figure 2:
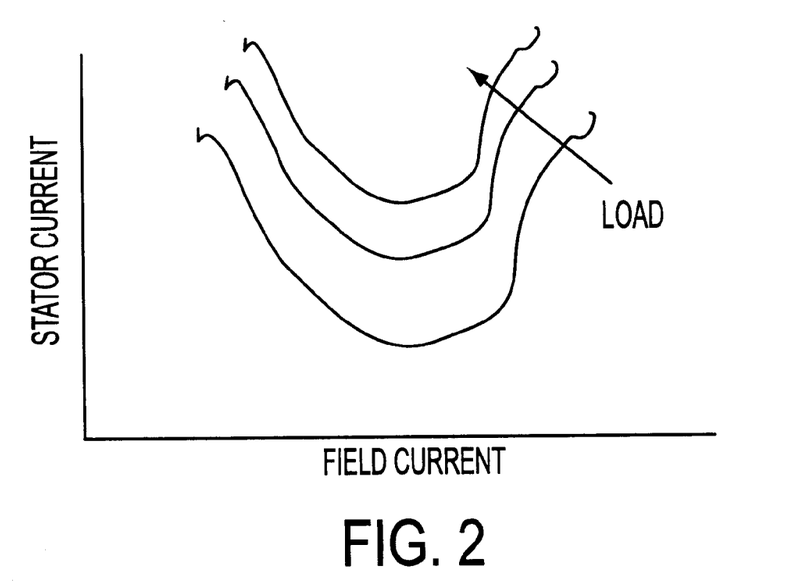
FIG. 2 shows stator current versus field current for a synchronous AC motor.

The synchronous AC motor has the desirable characteristic that its power factor can be varied over a wide range merely by changing the field excitation. With a weak field the motor takes a lagging current. Referring to FIG. 2, if the load is kept constant and the excitation increased, the current decreases and the phase difference between the voltage and current becomes less until the current is in phase with the voltage and the power factor is unity. The current is then at its minimum value. Further increase in field current causes the stator current to lead and the power factor to decrease. Thus underexcitation causes the current to lag; overexcitation causes the current to lead.

Figure 5:
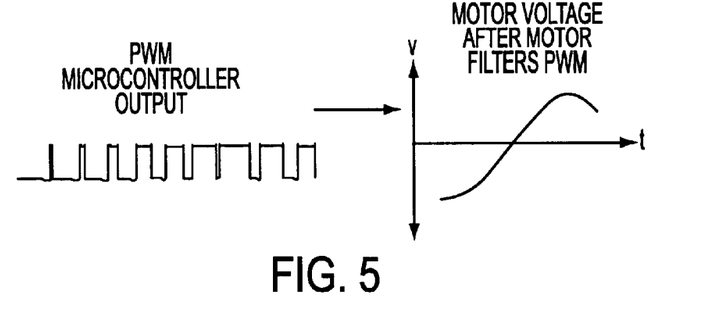
FIG. 5 shows diagrammatically how PWM pulses that are two sinusoidally weighted may produce current sinusoids in a motor.
Figure 6:
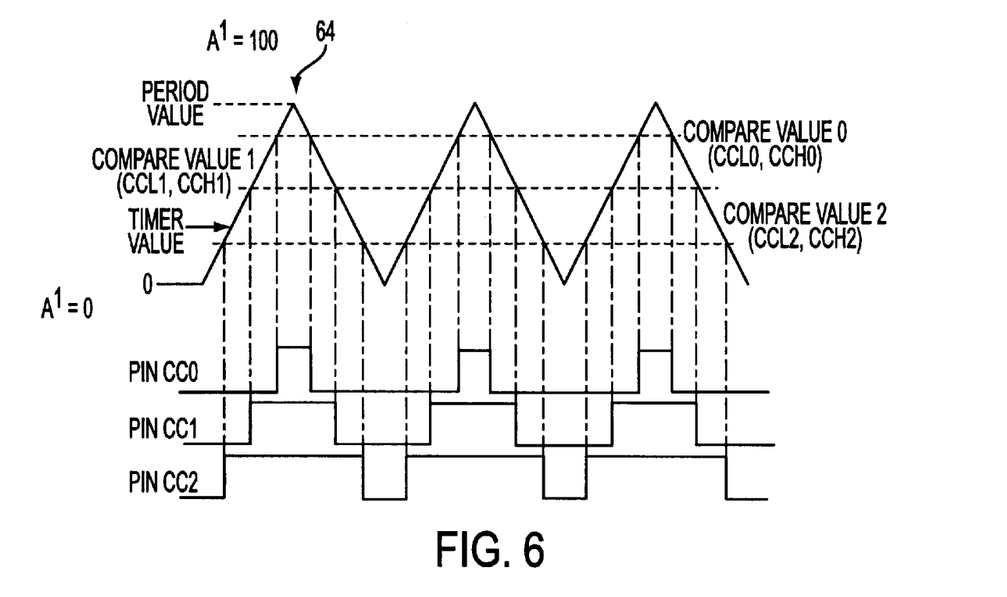
FIG. 6 shows how PWM pulses are generated using different compare values in a capture/compare unit of a microprocessor.

This over and under excitation can be accomplished using PWM signals generated by the microcontroller. A PWM signal of the type generated by the microcontroller in accordance with the present invention is shown on the left in FIG. 5. Referring to FIG. 5, it can be seen that three phase sinusoidal voltages are created with a signal having a very high constant frequency (compared to the frequency of the desired sinusoid) and a sinusoidally weighted duty cycle. This method of sinusoidal PWM can be referred to as SWPWM. SWPWM can be implemented in the microcontroller by placing sinusoidally weighted values into three compare registers of a microcontroller compare unit 34 (FIG. 1). The compare unit contains a timer and several compare registers configured to create variable duty cycle PWM signals. When the timer value is the same as the compare register value, an output pin is either pulled high or low. So the duty cycle of the output signal follows the compare value linearly. Some units have three compare registers and a timer that can count up from 0 to any specified 16-bit "period" value. When the timer reaches the period value, it reverses direction and counts down to 0. This is useful for generating center aligned PWM signals as shown in FIG. 6. Thus, when the compare values are reached, the PWM signal is toggled on or off as shown. When these pulses are filtered by the motor windings a continuous sine wave is seen as shown on the right in FIG. 5.

SWPWM has the advantage of requiring very little calculation (assuming look-up tables with the appropriate values are used). Each of the three phases can be made to generate a sinusoid that is 120 degrees out of phase. The sinusoidal phase voltages generate sinusoidal line-to-line voltages and sinusoidal line-to-neutral voltages when connected to a balanced star connected load. Since all of the voltages are sinusoidal, algebraic relations can be used to scale the generated voltages so that lengthy multiply instructions are avoided.

The sine waves generated by the compare unit have a specific frequency (which is essentially the interrupt rate of compare timer) as well as "amplitude". Amplitude in this instance is the percent of total period of the base frequency. For example, a sine wave with 100% amplitude would vary the PWM signal sinusoidally from near zero width to the maximum width. A sine wave with 50% amplitude would vary the PWM signal sinusoidally from near zero width to approximately 50% of the possible width.

The synchronous AC motor may be accelerated and decelerated without difficulty at any speed provided the power supply and resulting magnetic field is of sufficient strength. In practice, however, a power supply will always have a limited strength due to size and heat considerations and the magnetic field will be limited according to the type of rotor magnet employed. In such instances it is desirable to limit or tune the degree of acceleration and deceleration according to the motor. The present invention includes an optimal method of tuning and controlling the acceleration/deceleration.

In general, the energy required to keep a blower (or fan) in motion is the sum of the energy imparted to the air, the energy the energy dissipated by the frictional resistance of the bearing's and the energy lost to heat (current losses). A 4$^{th}$ term $E_{Sync}$ has also been added to indicate the additional energy (current) which is required when fields do not synchronize as was seen previously in FIG. 2.

$$E_{Total} = E_{air} + E_{Frictional} + E_{Heat} + E_{Sync} \quad [1]$$

The impeller itself stores kinetic energy as can be seen below $$E_{Impeller} = \tfrac{1}{2}I\omega^2 \quad [2]$$

Figure 3:
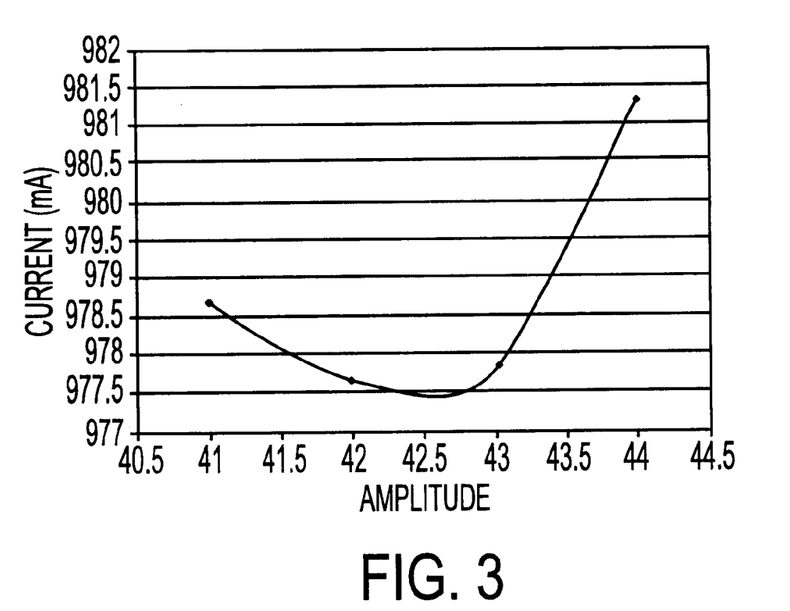
FIG. 3 shows average winding current versus raw amplitude for an actual blower/motor.

Here I is the moment of inertia of the impeller and ω is the circular frequency of rotation. The amount of energy imparted to the air is also a function of the impeller speed.

$$E_{air} = \text{func}(\omega^2) \quad [3]$$

where w is again the frequency of rotation. During acceleration energy is added to the system increasing the kinetic energy of the blower over a given period of time. We can therefore calculate the amount of power required to accelerate at a constant rate from frequency 1 to frequency 2 as:

$$P = \tfrac{1}{2} VI = (E_1 - E_2)/\Delta t < L \qquad [4]$$

where L is a limit given by the power supply and $E_{1,2} = E_{air} + E_{impeller}$. This power of course does not include losses and assumes correct phasing of the stator and rotor. If a system is designed to have minimal frictional and heat losses then motor synchronization is the single most important "loss" factor. If the blower is under or over driven the field generated by the motor may move out of phase with the driving field resulting in a higher dissipation of current and thereby energy. In general when a blower is driven at a given frequency as shown in FIG. 3, there exists an amplitude of the driving sine wave that results in a minimum current.

Figure 8:
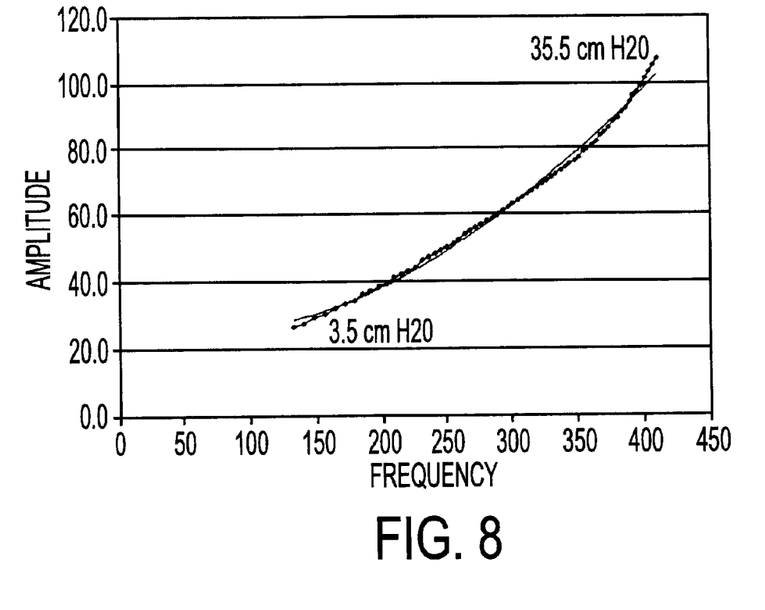
FIG. 8 shows raw amplitude as a function of frequency. Raw amplitude is a single compare value loaded into a compare register which can have values between 0 and the maximum period value which in this case is 120.

We can therefore create a table of frequencies and their associated minimum amplitude values as shown in FIG. 8. This will typically fit a parabolic curve, that is, amplitude will be a function of the square of the frequency. It is therefore clear that the frequency-amplitude function is nonlinear.

Figure 9:
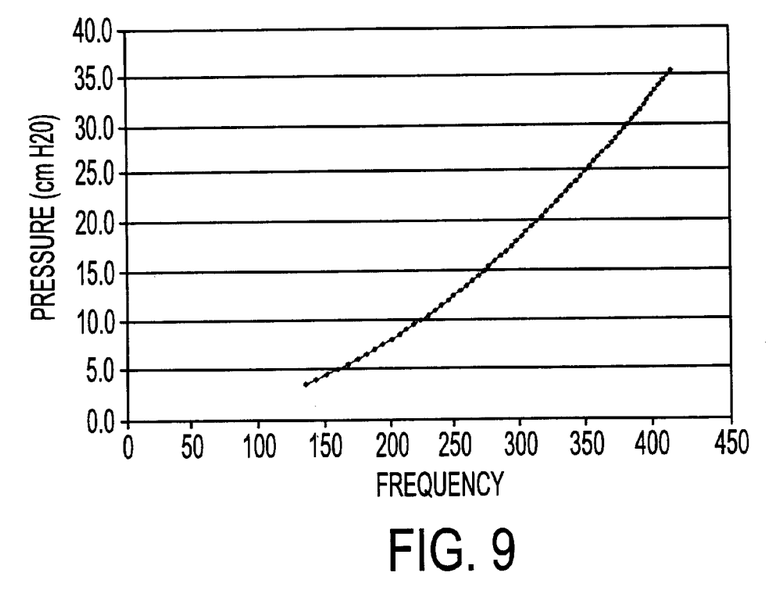
FIG. 9 shows pressure as a function of frequency for a typical centrifugal blower.

As an aside it should be mentioned that frequency is what gives rise to pressure as shown in FIG. 9. This is also generally not a linear function but due to blower inefficiency additional frequency is required to obtain the higher pressures resulting in a nonlinear curve similar to that shown in FIG. 9 which was generated using a constant flow of 45 LPM. We have therefore recognized that pressure, frequency and optimal amplitude are inter-related. Current and energy are directly linked to amplitude.

Figure 10:
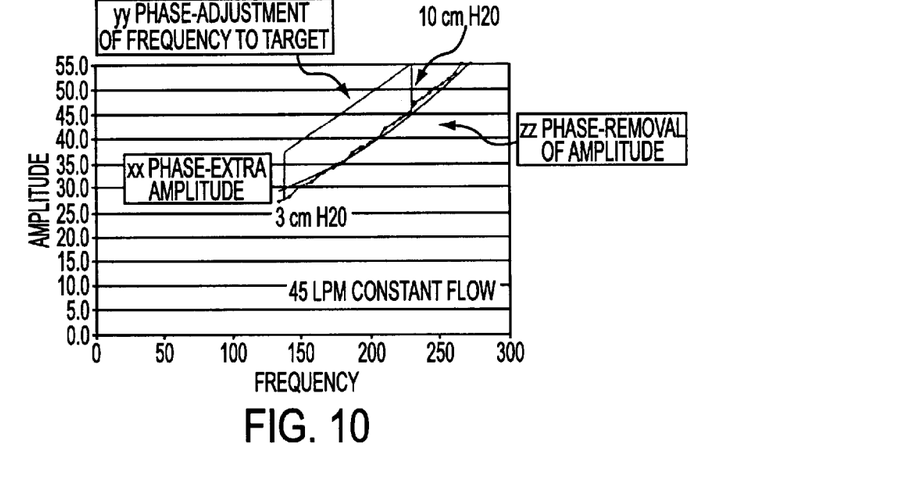
FIG. 10 shows a 3-step process of acceleration according to the present invention.

The process of acceleration or deceleration involves moving from one amplitude-frequency combination to a second frequency-amplitude combination as shown in FIG. 10. In accordance with one aspect of the invention, this is accomplished using a three-step process. Extra amplitude is first added to the motor so as to lessen the possibility of desynchronization (xx phase), amplitude and frequency are then increased until the frequency reaches the target (yy phase) and finally the extra amplitude is removed (zz phase).

Although the process of adjusting amplitude and frequency has been drawn as a continuous process, typically frequency and amplitude have finite integer values when produced by a modern microcontroller. Consequently, both amplitude and frequency are adjusted by the microcontroller in a series of "steps'. There therefore arises the question of how best to move from one amplitude frequency pair to another.

In accordance with the preferred embodiment of the present invention, the question is solved by programming the microcontroller to use the Bresenham algorithm. Briefly stated in words, the variable with the highest degree of discretization is adjusted in unitary increments each loop iteration. The second variable is adjusted in unitary increments at regular intervals based on the slope between the two points.

In the current context, "x" can be thought of as frequency and "y" as amplitude. We wish to move between x1 and x2 (i.e. from frequency 1 to frequency 2 which correspond to pressures 1 and 2) and correspondingly change the amplitude "y" from y1 to y2 in a linear or optimal fashion.

Pseudocode for this algorithm is given below. The portion in bold is preferably contained within the routine to set the new pressure. The italicized portion is preferably contained within a timer interrupt routine that adjusts frequency and amplitude at regular time intervals (e.g., every 1/4000 sec).

Listing 1
1. LinearAcceleration(x1,y1,x2,y2)
2. {
3. //x2 is assumed greater than x1 which is true for acceleration
4. If(y2>y1) {yincr=1} else {yincr=-1}
5. dx=x2-x1;
6. dy=abs(y2-y1)
7. d=2*dy-dx
8. aincr=2*(dy-dx)
9. bincr=2*dy
10. x=x1;
11. y=y1;
12. SetSpeedAmplitude(x,y)//i.e. feed the amplitude and frequency to the motor
13. for(x=x1+1; x<=x2;x++)
14. {
15. if(d>=0)
16. {y+=yincr; d+=aincr;}
17. else
18. {d+=bincr;}
19. SetSpeedAmplitude (x,y)//i.e. feed the amplitude and frequency to the motor
20. }
21. }

It should be noted that this algorithm assumes that x2 is greater than x1 and y2 greater than y1. This is true for acceleration. For deceleration y1 is greater than y2 and x1 is greater than x2. The formulas for dx and dy are reformulated as x1-x2 and y1-y2 so as to yield positive numbers.

A more detailed explanation of the above pseudocode with reference to line numbers is as follows:

Line 1 is a function statement which passes in the starting frequency x1, the ending frequency x2, the starting amplitude y1 and the ending amplitude y2. The algorithm assumes we are in quadrant 1 where x and y are both greater than 0. It is further assumed that the slope of the line we are to draw is less than 1. In our particular case this will be true insofar as the range of amplitudes (the y's) is less than the corresponding range of frequencies (the x's). The slope is delta y/delta x (dy/dx) so we meet the criteria for using this algorithm as written. The algorithm can be used in other octants by transformation. For example if the slope is greater than one (i.e., more amplitude values than frequency values) we would have swapped x and y.

In Line 4 we increment amplitude (and frequency by implication) in unitary units. The "if" statement in line 4 would account for deceleration.

Line 5 calculates the range of frequencies we will cover in our step. This assumes we are accelerating (i.e., x2>x1). If we decelerate, dx must be x1-x2. The differences dx and dy are always positive.

Line 6 calculates the range of amplitudes.

Line 7 calculates the so-called error variable. This may be set to "2 * dy" rather than "2*dy-dx" to force an immediate increment of the amplitude during the looping.

Lines 8 and 9 are the error variable increments.

Lines 10 and 11 are initializations for the loop (lines 13–20).

Lines 13–20 contain the essence of the algorithm. At every step there is an increment of frequency (x) since the range of that variable is the greatest, however, periodically at set intervals there is an increment of amplitude (y). This is based on the error variable "d". If the value of d is positive we increment y and add aincr to d, otherwise we just increment x and add bincr to d.

Note that dy will always be positive and dx will always be positive BUT dy will always be smaller than dx so aincr will be negative and bincr will be positive. By way of example, let's assume that the slope is dy/dx=⅓. In such an instance aincr=−2 * bincr. =−4 dy. The error variable will become positive every $3^{rd}$ time and you will increment y once for every three x increments.

In the instance where the range of y values is less than the range of x values you will generally step y by one (plus or minus). In an exemplary embodiment, an outlet gas pressure of 4 cm $H_2O$ corresponds to a blower frequency of about 148 Hz. Accelerating to 30 cm $H_2O$ would involve changing the blower frequency to about 380 Hz so you have a range of around 230 Hz. The corresponding amplitudes (the y values) go from 5 or 6 to around 80, so every 3 Hz you would step one amplitude unit. Keeping in mind the relative ranges of x and y values, the real purpose of the Bresenham algorithm is to come to the conclusion of the last sentence, that is, for every n frequency (x) steps you should step one amplitude (y) unit.

We should remark that as a variation on the above it is possible to step two or more frequency units at a time as long as amplitude (y) is also changed an equal number of units at a time. During deceleration which requires less energy than acceleration it is desired to decrease the speed faster so as to improve the work of breathing. In a preferred embodiment, this is accomplished by stepping two frequency units every given time interval. This currently allows achievement of rates of about 0.75 ms/Hz. By way of contrast, during acceleration with the same power supply, a rate of about 1 ms/Hz is currently achieved.

Figure 11:
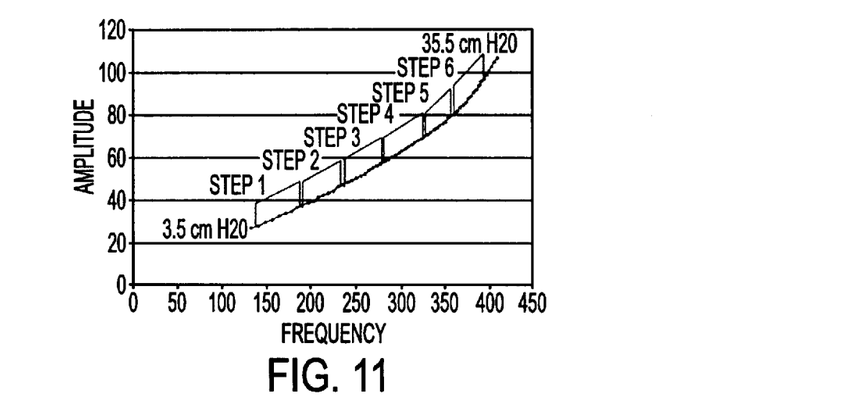
FIG. 11 shows how acceleration over a large range of frequencies may be accomplished in a quasilinear manner using a stored lookup table of raw amplitude and frequency values.

This algorithm would itself be optimal if the relationship between amplitude and frequency were to be linear. Unfortunately this relationship is not, but we can calibrate and store the optimal frequency-amplitude table. Using this information we can therefore proceed in a quasilinear or incremental fashion in one embodiment approximating the frequency-amplitude curve by a series of line segments as shown in FIG. 11. The advantage of this approach is that $E_{sync}$ becomes a minimum value thereby reducing the possibility of desynchronization for a given power supply size.

A second method of proceeding is to program the microcontroller to use a coordinate transformation such that the raw amplitude (essentially the compare value shown in FIG. 6) is mapped to a linearized quantity, A prime (A'), which has as its values 0 (the value at which no motor movement takes place) and 100 (the value at which the stator is maximally energized). The amplitude-frequency relationship of FIG. 11 would then become a straight line and it would be possible to proceed from a low pressure to a high pressure in a single step. In the basic program below, an 8-bit period value is used (which is the raw amplitude). The counter counts from 0 to 64 and back down as shown in FIG. 6 generating symmetrical on time pulses. Compare values are loaded into the compare registers approximating a sine wave of n parts (12 are assumed here). The maximum transformed amplitude (A') of the sine wave is generated by the "j" loop given below and is equal to "j% * stepamp#+ offset#". An offset equal to 5% of the total period (raw amplitude) is subtracted from the period, because it has been determined empirically that no movement of the rotor can take place without some minimal energization of the stator. This percentage will differ depending upon the motor design, weight of the rotor, etc. Therefore in the preferred embodiment, A' will comprise compare values all of which are associated with rotor movement.

Listing 2

```
pi# =3.14159265359#
period# = 64#     'Period value in FIG. 3 (raw amplitude)
offset# = 3.2#    '5% of the base value
nparts = 12#      'a 12 part sine wave approximation
da# = 2# * pi# / nparts#
amp# = offset#
stepamp# = (period# − 3.2#) / 100#
OPEN "PH12st_7.txt" FOR OUTPUT AS #1
FOR j% = 0 TO 100   'Zero is no movement; 100 is all on
   a# = da# / 2
   IF j% = 0 THEN amp1# = 0 ELSE amp1# = amp#
      FOR i% = 1 TO 3 'Generate A' for each of 3 phases
      PRINT #1, USING "###"; SIN(a#) * amp1#;
         IF i% < 3 THEN PRINT #1, ",";
         a# = a# + da#   'Increment by 120 degrees
      NEXT
   amp# = amp# + stepamp#   'Get next amplitude
NEXT
```

When this transformation is made the optimal amplitude for any given frequency can be determined from a simple relationship.

$$A'=\text{Amplitude Coefficient/Frequency-offset}$$

Figure 4:
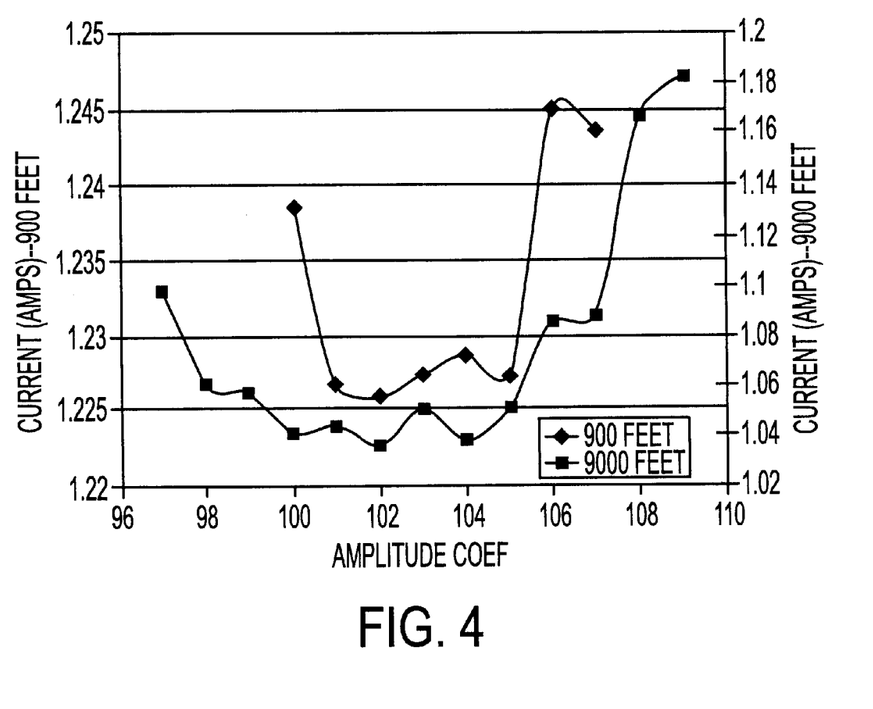
FIG. 4 shows current versus the amplitude coefficient at two different altitudes demonstrating that an optimal amplitude coefficient is altitude independent.

The amplitude coefficient is determined by finding the minimum current at a constant frequency (e.g. 320 Hz) under a constant load (i.e., constant flow rate) as shown in FIG. 4. This will be a constant at all altitudes (i.e., air densities) up to 9000 feet provided the flow rate is kept constant even though average energy dissipation decreases as density decreases. As flow rate increases the optimal amplitude coefficient will also slightly increase. Consequently a flow rate should be chosen for amplitude coefficient calibration which is typical for the operation of the device. For the preferred embodiment this is 45–60 liters per minute (LPM) which is slightly above a 4 mm nominal bleed hole leak rate (face masks are designed with exhaust ports or bleed holes so there is always some flow) and is therefore approximately what would be produced by a patient quietly breathing. Since flow is monitored using a flow meter, the amplitude coefficient could also be changed as a function of flow but this is generally not required since the change of amplitude coefficient with load is small.

Once the relationship between A' and frequency is known, the Bresenham approach may be used to conveniently and optimally change from the first frequency to the second frequency with corresponding values of $A_1'$ and $A_2'$ allowing the power supply to be optimally sized. An issue that remains is how the extra amplitude (xx) is determined. It has been found that if the extra amplitude is too small, the rotor will lose synchronization during acceleration. This may also happen if the extra amplitude is too large. To determine how much amplitude is required, an analysis of the motor current is required.

Figure 7:
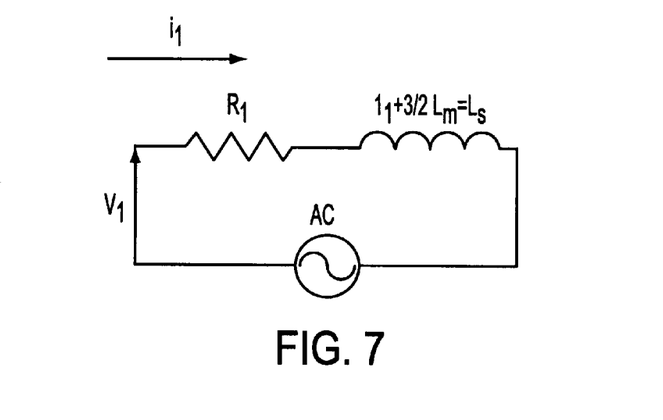
FIG. 7 is the equivalent circuit for an AC motor.

The equivalent circuit for a synchronous A/C motor is shown in FIG. 7. The solution to the equation for current for this circuit is:

$$i_f = \sqrt{2} I_t \sin(\omega t + \phi_1) + A e^{-(t/T)}$$

Here the time constant is given as the ratio between the synchronous inductance and the coil resistance ($L_s/R_l$). Therefore if the initial acceleration is "slow" the second term can essentially be neglected and transient effects ignored. If acceleration is rapid, the second term may be ignored if the time constant is large or sufficient time passes that transients are no longer of consequence. Making the time constant large can be accomplished by increasing magnetic strength of the rotor through the use of rare earth magnets and secondly by increasing the strength of the electric field of the stator. The electric field may be increased by appropriate increases of the amplitude (A').

Figure 12:
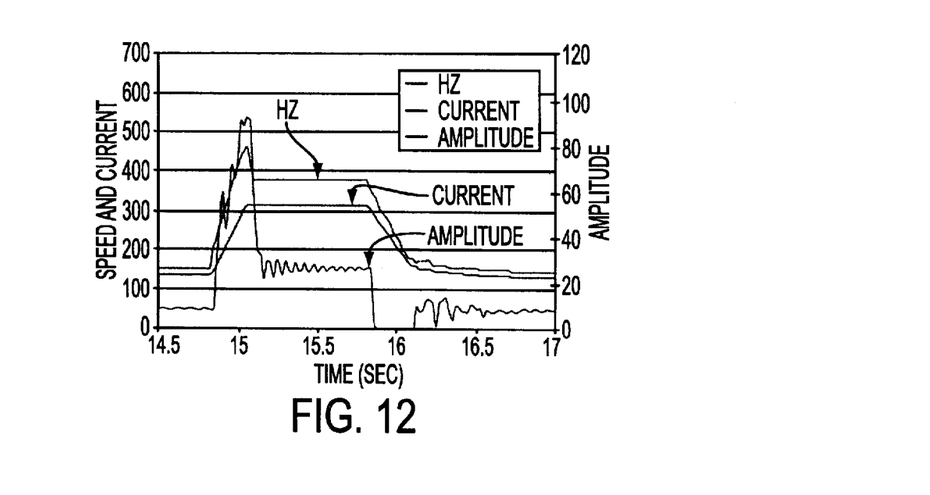
FIG. 12 shows current resulting from an acceleration process and in particular how the current "rings" due to the change of speed.
Figure 13:
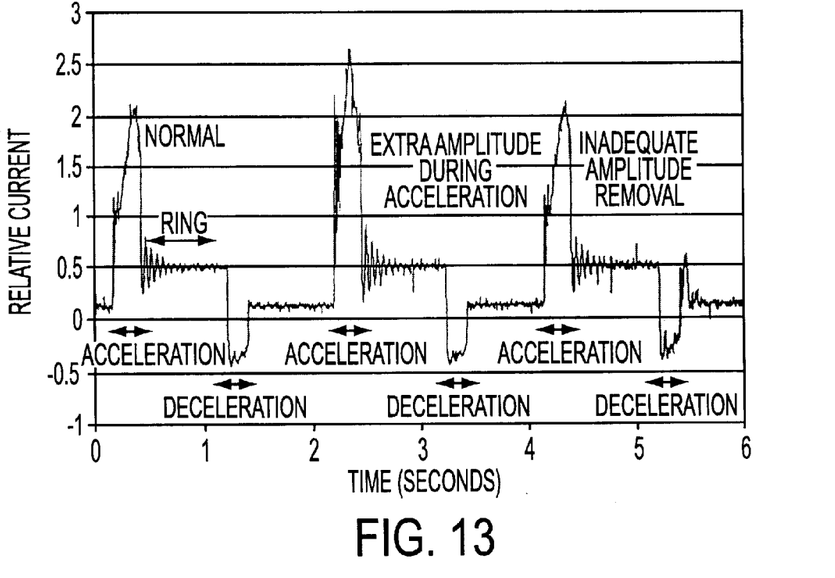
FIG. 13 shows how acceleration constants and breaking parameters can be visually tuned by examining the current-time waveform during acceleration and deceleration.

FIG. 12 shows a typical "ringing" of the current as a result of the acceleration process. The ringing is an electromechanical phenomenon, which results during acceleration when a system perturbation causes the magnetic field momentarily to lead the rotor rotation and then subsequently lag the rotor rotation. The alteration between lead and lag continues until the rotor is again perfectly synchronous with the field rotation. For a given motor design this will have a particular period. The value of "xx" is chosen empirically so as to minimize the amplitude of the ring which begins at the end of acceleration and minimize the total current during acceleration. FIG. 13 shows a correctly tuned curve on the left while the middle shows the effect of too much extra amplitude. Too little extra amplitude simply causes the system not to work. The amount of extra amplitude is proportional to the rate of acceleration and frequency. Consequently a multiplicity of constants are defined such that:

Additional A' ("xx")=frequency/acceleration constant

At a high rate of acceleration (e.g., 1 ms/Hz) a typical acceleration constant is 12. At lower rates of acceleration (e.g., 1.25 to 2.50 ms/Hz) a typical acceleration constant is 15. At the lowest rates of acceleration (e.g., 4 ms/Hz) a typical acceleration constant is 38. These tuned acceleration constants are stored in a table indexed by the rate of acceleration. This table is accessed as part of the acceleration process as will be described later.

It should be remarked that the ringing of FIG. 12 can also be minimized by feedback control of current. The average current from the three windings is filtered and scaled such that one A/D current unit is equivalent to two amplitude units or put another way an increase of one unit of amplitude results in approximately one half current units.

Figure 17:
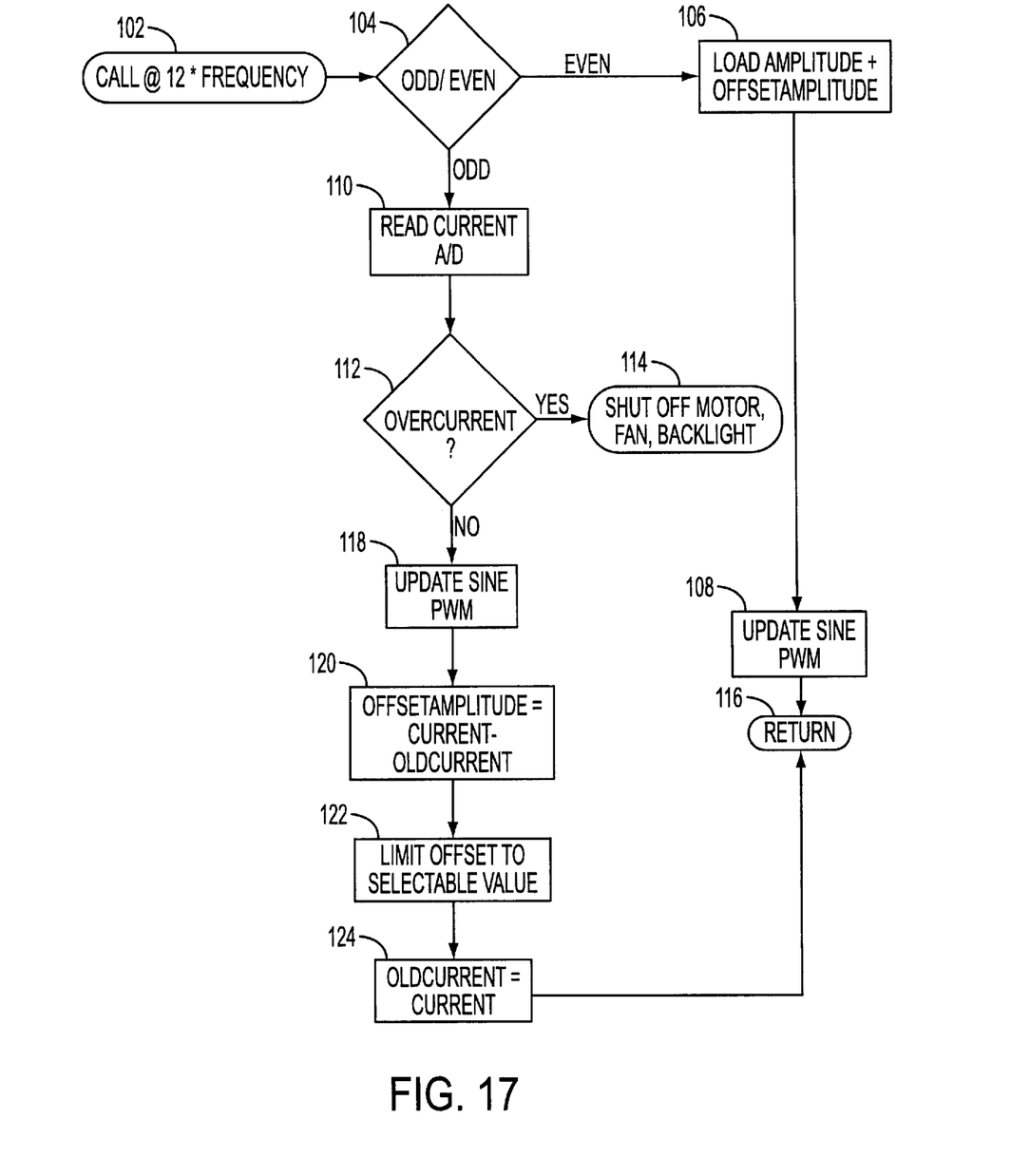
FIG. 17 shows a method of using feedback of average current so as to minimize current "ring" in accordance with the present invention.

This represents a 50% proportional gain in the feedback control circuit where amplitude is used to minimize current. Consequently as shown in FIG. 17, a current feedback scheme may be preferentially utilized by the highest priority interrupt to reduce the amount of ringing during an acceleration, pressure control and/or deceleration process. Referring to FIG. 17 at 102, the routine illustrated is called at a rate twelve times the frequency of the motor in order to produce a sine wave consisting of twelve parts; however, other multiples of the frequency can be used. A determination is made at 104 if the call is odd or even. During each even call we reload the amplitude plus a calculated offset amplitude as indicated at 106 and update the compare registers with the next component of the 12-part sine wave as indicated at 108. During each odd call the current A/D channel is read as indicated at 110 and a check is made at 112 to see if the current is over the specified limit for a specified period of time. If it is, we turn off the motor and peripheral devices as indicated at 114 and return to the calling routine at 116. If it isn't, the compare registers are updated with the next component of the 12-part sine wave at 118 and a new offset amplitude is calculated as the difference between the present current value and the last current value at 120. This offset amplitude is limited to a selected value at 122. The old current is then set to the present current at 124 and we return as indicated at 116.

The other implication of the ring shown in FIG. 12 is that it is preferable to space speed adjustments by some minimum amount in order to allow the current perturbations to die down. Generally speed changes are due to either a breath (inhale or exhale) detection and/or pressure feedback adjustment. Breath detections produce speed changes at maximum acceleration and deceleration rates (e.g., about 1 ms/Hz) on an infrequent basis while pressure feedback adjustments change speed at moderate rates (e.g., about 4 ms/Hz) albeit more frequently. In accelerating at a fast rate, additional amplitude (A') is added to cause the blower to track the speed change. Consequently a spacing of about 20–40 ms is appropriate. Pressure feedback adjustments add less amplitude and change frequencies by smaller amounts. Consequently additional A' is added. Spacing of about 60–100 ms is therefore appropriate.

Figure 14:
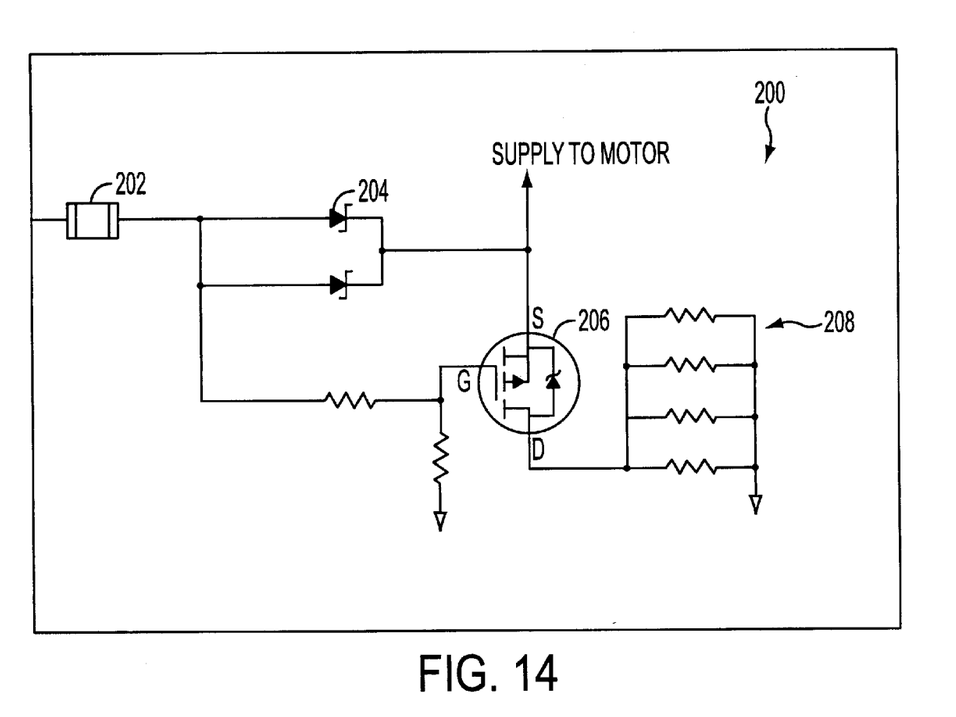
FIG. 14 shows the design of a multiple range switching power supply and how voltage may be shunted back to the power supply during deceleration.

FIG. 13 also shows the proportion of the current time curve attributable to the deceleration process. A hardware modification is useful and a software modification is required to deal with deceleration. With regards to hardware, the secondary of the switching power supply 26 (FIG. 1) preferably has two voltage taps. One provides 12 Volts needed to operate the processor and analog circuitry. The other provides 27.5 Volts needed to drive the blower motor. The power supply regulates the 27.5V supply only. The 12 Volt supply depends on the continuous operation of the 27.5 V supply. If the 27.5 V supply quits then so will the 12 V supply. During deceleration the motor acts as a generator and attempts to increase the 27.5V supply. Normally this would cause the switching regulator to stop, resulting in loss of the 12V supply. To prevent this, a clamp circuit 200 (FIG. 14) can be added that detects the motor voltage and shunts the excess to Ground. This modification allows the deceleration scheme to operate with a multiple output switching power supply. During operation, voltage is supplied to the motor circuit through fuse 202 and diode 204. During the deceleration period, the motor creates excess voltage at the anode of diode 204 causing it to be reverse biased. As the reverse bias reaches approximately 3 volts, transistor 206 will begin conducting current through resistor array 208. Resistor array 208 will be heated, thus dissipating the energy created by decelerating the motor.

With respect to software, amplitude is subtracted from the nominal amplitude at the start of deceleration (the breaking parameter). A correctly tuned value results in a square looking current curve at the end of deceleration when the nominal amplitude is restored (leftmost curve in FIG. 13). If insufficient amplitude is removed, the current produces an overshoot at the end of deceleration (rightmost curve in FIG. 13). This overshoot if sufficiently large can cause the motor to desynchronize. Again the amount of amplitude which needs to be removed is speed dependent. At the highest rate of deceleration (e.g., ¾ ms/Hz) 27 A' units must be removed. At slower rates of deceleration (e.g., 4 ms/Hz) only 6 A' units must be removed. A table of these tuned breaking parameters indexed by rate of deceleration can be stored and accessed by the microprocessor during a speed change process.

During the process of acceleration or deceleration, there is a finite probability of the rotor becoming desynchronous with the rate of rotation of the field. This may occur due to a sudden burst of air (e.g. a sneeze) which dramatically increases rotor resistance and/or a mechanical obstruction which prevents rotation. In the preferred embodiment it is desirable to detect such a condition, shut the motor down and attempt a restart. To accomplish this both motor current and power supply voltage are digitized. If a desynchronization occurs, motor current will increase dramatically. If it stays above a settable maximum level (see FIG. 17 at 112) for more than a settable number of conversions the motor, the cooling fan and LCD backlight all turn off (see FIG. 17 at 114). Similarly if the power supply voltage drops below a settable level, the motor and accessory devices are also turned off. Finally if the detected current is greater than the amplitude (for a 50% gain system this means that current is twice what it would normally be) for a measurable period of time then we also shut off the unit. This last rule is useful for lower frequencies where current may not exceed the settable maximum value but where upon desynchronizing the current is still too high and could result in damage to the stator if the motor isn't turned off.

Figure 15:
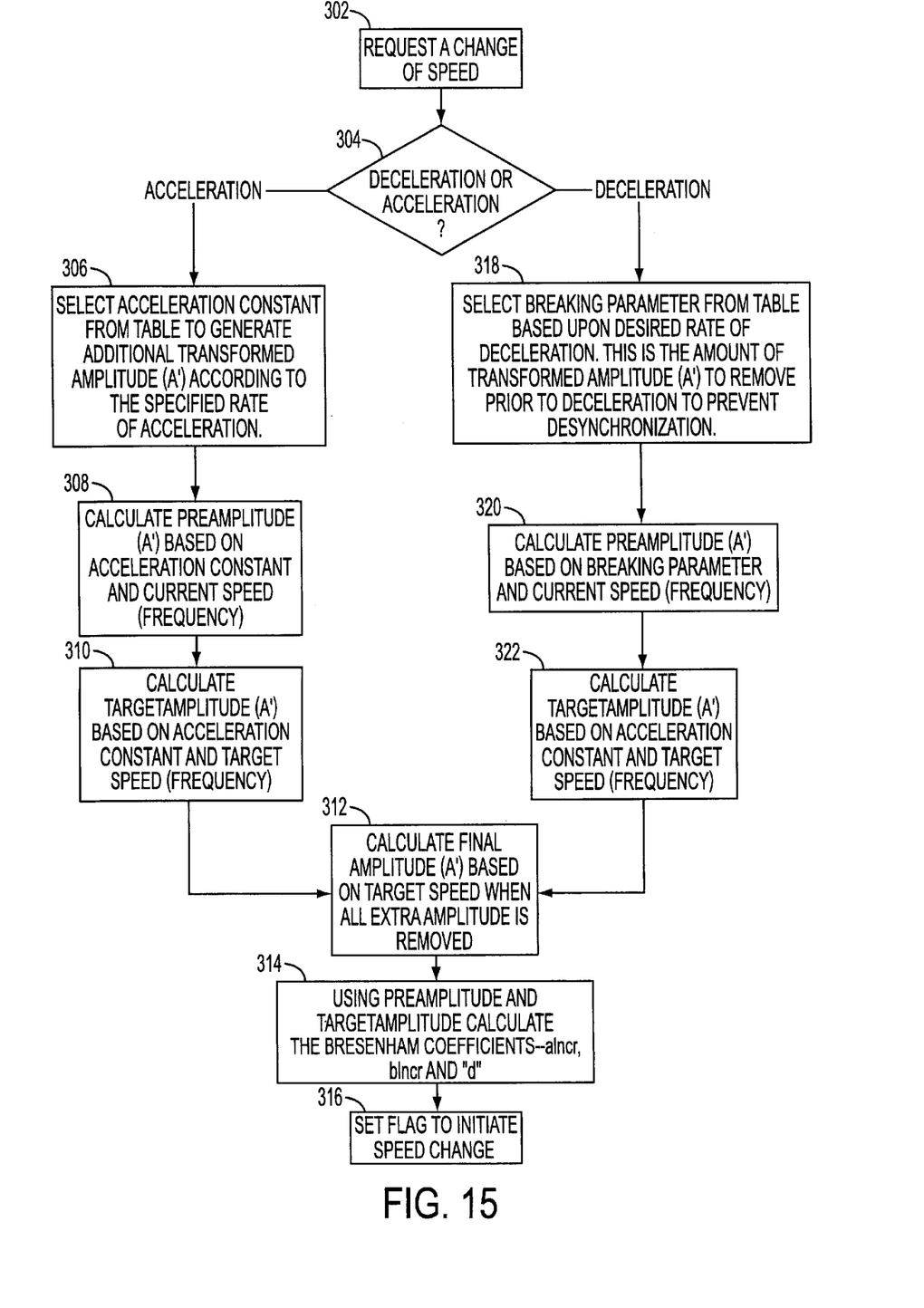
FIGS. 15 and 16 show the step-by-step process of how acceleration and deceleration can be implemented in accordance with the present invention.
Figure 16:
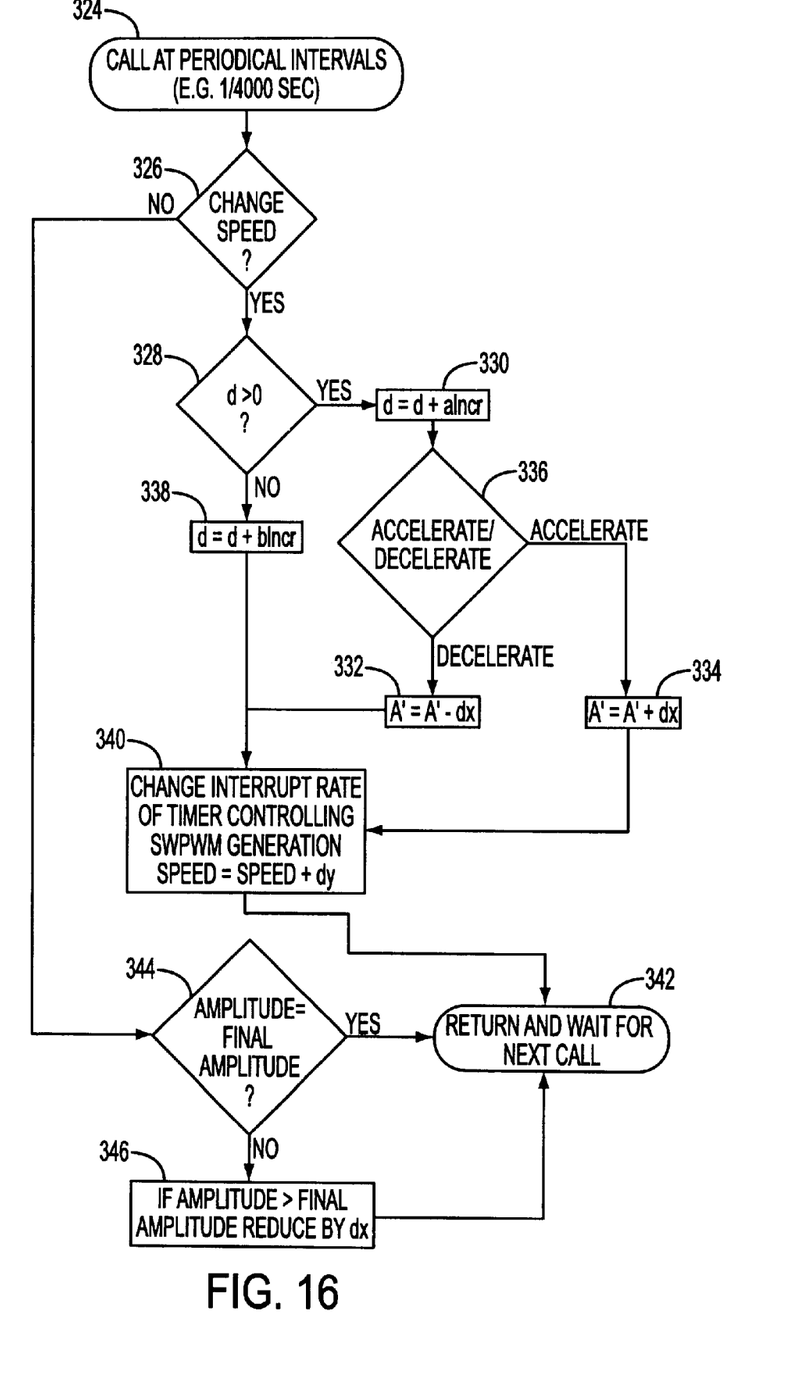

FIGS. 15 and 16 show in diagrammatic form a step-by-step process by which the invention can be embodied. When a speed change is requested at 302 a decision is made at 304 as to whether the request constitutes an acceleration or deceleration. If an acceleration is chosen then an acceleration constant of the type disclosed earlier is chosen from a table which is indexed by the acceleration rate at 306. Using this constant, the preAmplitude and targetamplitude are calculated at 308 and 310, respectively, based the current speed and the target speed (i.e. frequency). In addition a final amplitude is calculated at 312 based upon the target speed at steady state (i.e. after acceleration is complete). From the current and target speeds and the preAmplitude and targetAmplitude, the Bresenham coefficients alncr, blncr, and "d" can be calculated as indicated at 314. At this point the speed change is initiated by setting a flag at 316 which is read in one of the fast timer interrupts. Similarly if deceleration is chosen, an appropriate breaking parameter is read from a table which is indexed by the speed of deceleration as indicated at 318. Then the preAmplitude and targetamplitudes can be calculated using this breaking parameter. And then the final amplitude and Bresenham coefficients can be calculated as before.

Referring now to FIG.16, once the flag is set indicating a speed change, the main timer interrupt begins adjusting the speed and amplitude simultaneously as indicated at 324. If a decision to change the speed is made at 326, a decision is then made at 328 as to whether d (essentially the number of y direction adjustments made for each x direction adjustment) is greater than zero. If so alncr is added to d at 330 and then the amplitude is adjusted at 332 or 334 depending upon whether acceleration or deceleration is called for at 336. If d is not greater than zero, blncr is added to d at 338 until it does become greater than zero. At each iteration the frequency is adjusted by dy unit up or down depending upon whether acceleration or deceleration is occurring the interrupt rate of the timer controlling the SWPWM sine wave generation is adjusted at 340. At this point the interrupt returns as indicated at 342. If no speed change is called for then one asks at 344 whether the amplitude is equal to the final amplitude. If not, the amplitude is decreased at 346 until it equals the final amplitude. This is the final leg of the acceleration process shown in FIG. 10.

While the preferred embodiments of the invention have been disclosed in detail above, the invention is not intended to be limited to the embodiments as disclosed. Those skilled in the art may make numerous uses and modifications of and departures from the specific embodiments described herein without departing from the inventive concepts. For example, while the invention has been described in connection with treatment of sleep apnea, it will be appreciated that the invention can be used in connection with any type of respiratory therapy, where by "respiratory therapy" is meant any application where it is desirable to deliver a breathing gas to a user. While the blower and blower control circuitry are preferably contained within a single gas flow generating unit, it will be appreciated that they can be contained within separate units that communicate via an external connection. It will also be appreciated that various filters can be positioned at the gas inlet and/or the gas inlet or at any other location in the gas flow generator or the patient circuit. In addition to motor control, the microcontroller can be used for pressure analysis, leak compensation, and other functions related to delivery of a breathing gas to a user. Preferably, the gas flow generator includes a display 42 and controls 44 allowing an operator to monitor conditions and settings of the apparatus including, for example, outlet pressure, excess leak, tidal volume, and peak flow. If desired, the gas flow generator can include a communication port allowing an external computer to be linked to the system for remote display and/or control of the gas flow generator. The term "microcontroller" is used generically herein to refer to any suitable microprocessor, integrated circuit, computer, or circuit capable of inputting and outputting signals and performing motor control functions of type described herein. The terms "program memory", "memory" and "data storage" are used generically herein to refer to any type of electronic data storage device including, by way of example, read-only memory (ROM), programmable read-only memory (PROM), random access memory (RAM), magnetic storage devices, and optical storage devices.

What is claimed is:

1. An apparatus for delivering a breathing gas to a user comprising
    a blower having an alternating current (AC) motor and an impeller rotated by said AC motor to deliver a breathing gas to a user;
    a blower control system providing a motor control signal of variable frequency and amplitude to said AC motor, wherein frequency and amplitude of said motor control signal are adjusted periodically by said blower control system to cause operation of said AC motor to alternate between an inhalation mode wherein said impeller is rotated at a first speed generating an inhalation positive airway pressure and an exhalation mode wherein said impeller is rotated at a second speed generating an exhalation positive airway pressure.

2. The apparatus of claim 1, wherein said blower control system includes a microcontroller and said motor control signal is a pulse width modulated signal generated by said microcontroller.

3. The apparatus of claim 2, wherein said pulse width modulated signal has a sinusoidally weighted duty cycle.

4. The apparatus of claim 3, wherein said microcontroller includes a compare unit with a timer and a plurality of compare registers, and wherein said sinusoidally weighted pulse width modulated signal is created based on a comparison of a timer value with a compare register value.

5. The apparatus of claim 4, wherein said blower control system includes memory programmed to hold a table of sinusoidally weighted compare register values.

6. The apparatus of claim 4, wherein said compare timer has a variable interrupt rate defining a frequency of said pulse width modulated signal.

7. The apparatus of claim 2, further comprising a flow sensor generating a flow signal which varies in response to inhalation and exhalation by a user, and a trigger circuit providing a trigger signal to said microcontroller in response to said flow signal, said microcontroller adjusting the frequency and amplitude of said motor control signal to switch between said inhalation and exhalation modes in response to said trigger signal.

8. The apparatus of claim 2, wherein said microcontroller includes memory programmed to hold minimum amplitude values for a set of frequencies corresponding to specific gas pressures, and wherein said microcontroller retrieves a stored amplitude value from memory when switching from one frequency to another.

9. The apparatus of claim 2, wherein said blower control system changes the frequency and amplitude of the motor control signal by adjusting the frequency and amplitude in unitary increments based on a slope of frequency versus amplitude.

10. The apparatus of claim 2, wherein said blower control system changes the frequency and amplitude of the motor control signal using a Bresenham algorithm.

11. The apparatus of claim 1, wherein a first frequency and amplitude of said motor control signal cause said impeller to operate at said first speed and a second frequency and amplitude of said motor control signal cause said impeller to operate at a second speed, wherein said first speed is greater than said second speed, and wherein said blower control system increases the speed of said impeller from said first speed to said second speed by adding an excess amplitude to said motor control signal, increasing the frequency and amplitude of the signal based on a difference between the first frequency and amplitude and the second frequency and amplitude, and removing the excess amplitude.

12. The apparatus of claim 11, wherein the excess amplitude is equal to the ratio of the second frequency to an acceleration constant.

13. The apparatus of claim 12, wherein the motor control system includes memory programmed to hold acceleration constants for various frequencies.

14. A method of generating bilevel positive airway pressure for respiratory therapy using a gas flow generator having a blower powered by an alternating current (AC) motor, said method comprising the steps of:

applying a motor control signal having an amplitude and a frequency to the motor to produce a blower speed;

determining whether a speed change is required for the blower;

determining a target amplitude and a target frequency corresponding to a target speed; and adjusting the amplitude and frequency of the motor control signal until the amplitude and frequency correspond with the target amplitude and the target frequency, wherein one of the amplitude and frequency is incremented during a first interval and the other is incremented during a second interval which is a multiple of the first interval.

15. The method of claim 14, wherein the second interval is based upon a comparison of a differential change in amplitude and a differential change in frequency needed to move from the amplitude and frequency to the target amplitude and frequency.

16. The method of claim 14, wherein a Bresenham algorithm is used to adjust amplitude and frequency of the motor control signal.

17. The method of claim 14, further comprising the steps of adding excess amplitude before said adjusting step, and removing the excess amplitude after said adjusting step.

18. The method of claim 17, wherein the excess amplitude is equal to a ratio of the target frequency to an acceleration constant.

19. The method of claim 18, further comprising the step of retrieving the acceleration constant from a memory device.

20. The method of claim 14, wherein the applying step includes using a microcontroller to generate a pulse width modulated motor control signal having a sinusoidally weighted duty cycle.

21. The method of claim 20, wherein said microcontroller includes a compare unit, and wherein said adjusting step includes changing a timer interrupt rate in said compare unit to change the frequency of the pulse width modulated motor control signal.

22. The method of claim 21, wherein said adjusting step includes retrieving sinusoidal weight values corresponding to an amplitude from a memory device and placing the sinusoidal weight values in compare registers of the compare unit to change the amplitude of the pulse width modulated motor control signal.

* * * * *